US00PP11008P

United States Patent [19]

Kiyama

[11] Patent Number: Plant 11,008

[45] Date of Patent: Jul. 13, 1999

[54] 'LEUCOTHOË FONTANESIANA TRICOLOR'

[76] Inventor: Masaji Kiyama, 8688-119 Gudo, Nakamura Shi, Kochi Ken, Japan

[21] Appl. No.: 08/799,214

[22] Filed: Feb. 13, 1997

Related U.S. Application Data

[51] Int. Cl.[6] ..... A01H 5/00

[52] U.S. Cl. ..... Plt./226

[58] Field of Search ..... Plt./54.1

[56] References Cited

U.S. PATENT DOCUMENTS

P.P. 5,224 4/1984 Zebehazy ..... Plt./54

P.P. 5,229 5/1984 Zebehazy ..... Plt./54

P.P. 8,901 9/1994 Lawandowski et al. ..... Plt./54.1

P.P. 10,128 11/1997 Fincham ..... Plt./54.1

*Primary Examiner*—Elizabeth C. Kemmerer

*Attorney, Agent, or Firm*—Nikaido Marmelstein Murray & Oram, LLP

[57] ABSTRACT

A new distinct variety of *Leucothoë fontanesiana axillaris* having leaves of red, yellow and green. The plant is hardy against cold and seldom suffers from disease or insect damage.

3 Drawing Sheets

The present invention concerns a new and distinct variety of plant derived from a Leucothoë plant variety.

BACKGROUND OF THE INVENTION

Previously known varieties of Leucothoës include evergreen and leaf-losing shrubs, widely distributed in North and South America, the Himalayas, Japan and other countries. A few kinds are in cultivation. They belong to the Heath family, Ericaceae. Leucothoës bloom in spring and early summer.

Leucothoës are moundlike shrubs with arching branches. They grow 3 to 5 feet tall in four to five years, and older plants spread slowly from underground roots. Since Leucothoës bear thick foliage on branches that droop almost to the ground, they are excellent for use in front of older larger shrubs and trees that have become unsightly at the base. They also are useful as a ground cover on a shady bank. New shoots rising from the ground and atop older branches in early spring are a bronzy green; as summer advances and the stems elongate, the glossy 4- to 7- inch leaves become a rich dark green—only to turn to a reddish bronze in northern areas as cool weather arrives. In severe winters, the plants may lose some of their upper leaves. In summer, small flower buds form at leaf axils (the points where leaves join the stems) on the outer 2 feet of each arching cane. The following spring, the buds expand into 2- to 3- inch slusters of tiny white flowers that resemble lillies of the valley. The flowers hang gracefully beneath the canes, accounting for the plant's common name. The leaves, with or without blossoms, make attractive bouquets. The varieity Rainbow has leaves marked with creamy yellow; its new growth is pink.

Leucothoës require light to deep shade and a moist acid soil. If fast growth is desired, cottonseed meal or a rhododendron-azalea-camellia fertilizer can be scattered under the plants in early spring. After plants are well established, the biggest and oldest canes can be cut to the ground in very early spring; and this pruning will keep the plants looking young and healthy.

These shrubs thrive in acid loam and peaty soils, but, like most other members of the Heath family, they detest lime. Propagation is by sowing seeds in fine soil in a slightly heated greenhouse in March or in a cold frame in spring, or by taking cuttings in late summer or early fall. The cuttings are placed in a mixture of sand and peat moss in a closed frame or greenhouse propagating bench which is kept closed until the cuttings are rooted.

SUMMARY OF THE INVENTION

In accordance with the present invention, there is provided a new and distinct variety of Leucothoë. The most significant feature of the new and distinct plant variety of the present invention is that it exhibits leaves which are red, yellow and green. For this reason, the applicant proposes to name the new and distinct plant variety of the present invention "Leucothoë fontanesiana tricolor."

DETAILED DESCRIPTION OF THE INVENTION

Figure 1:
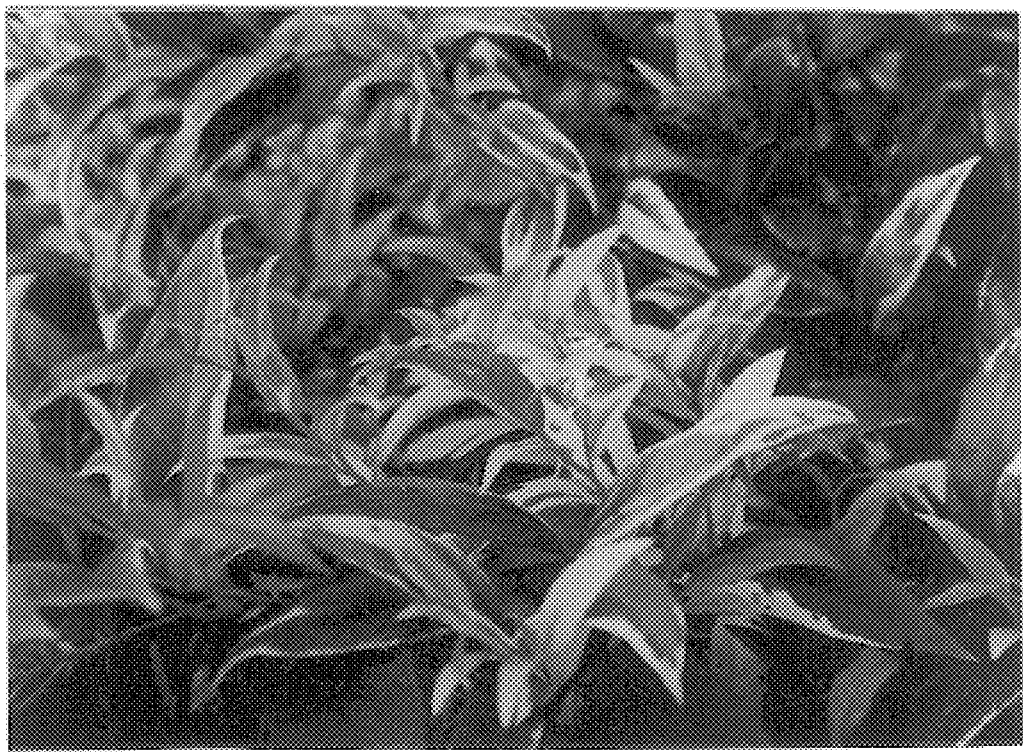
FIG. 1 shows matured *Leucothoë fontanesiana tricolor* of the present invention.
Figure 2:
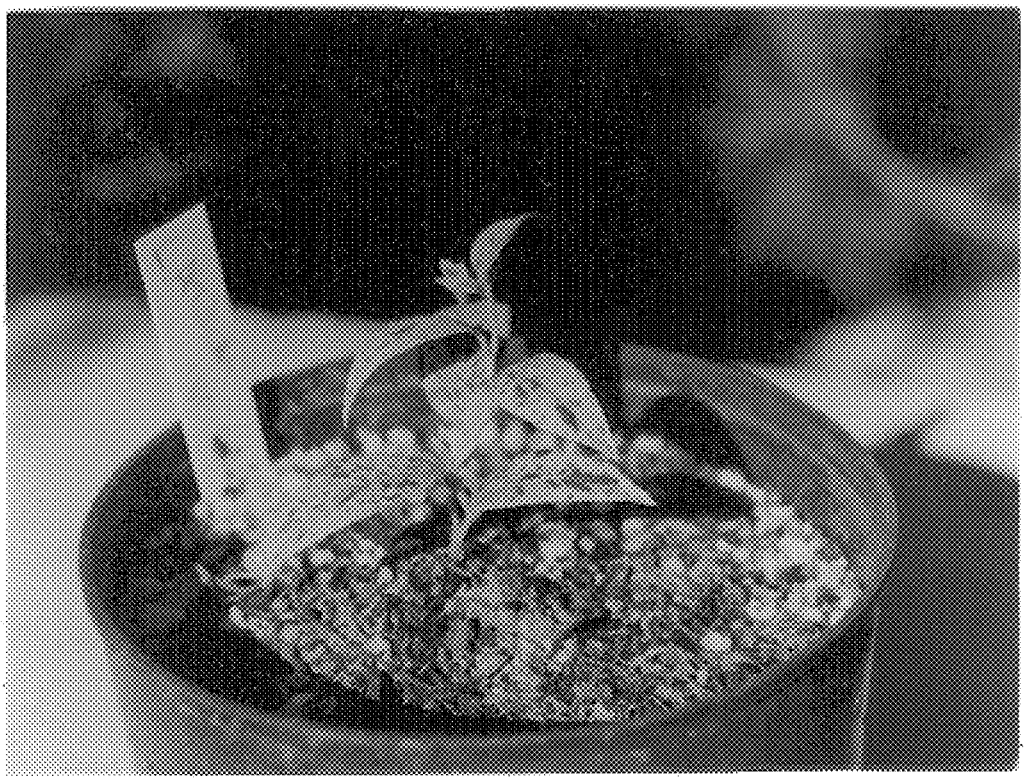
FIG. 2 shows *Leucothoë fontanesiana stardust*.
Figure 3:
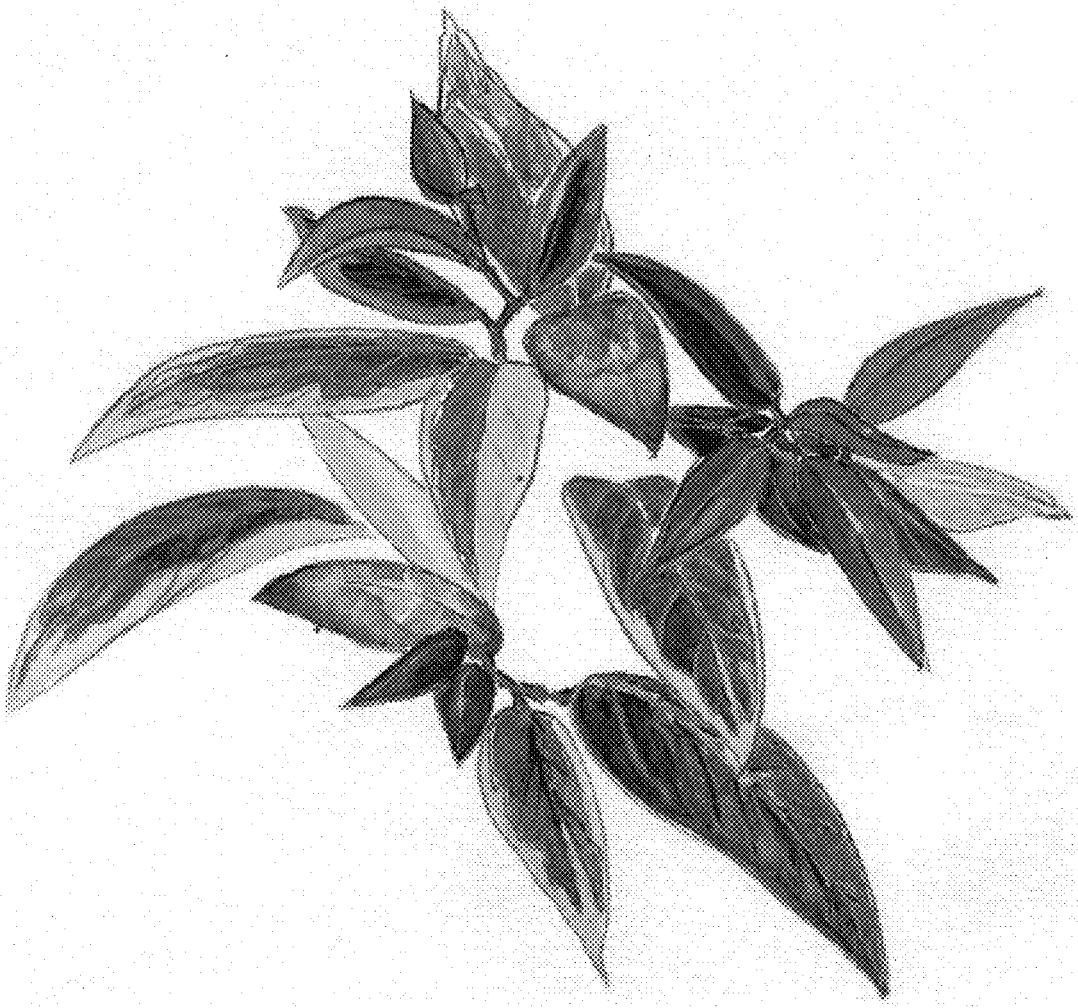
FIG. 3 illustrates a typical specimen of the new and distinct tricolored variety of the present invention.
Figure 4:
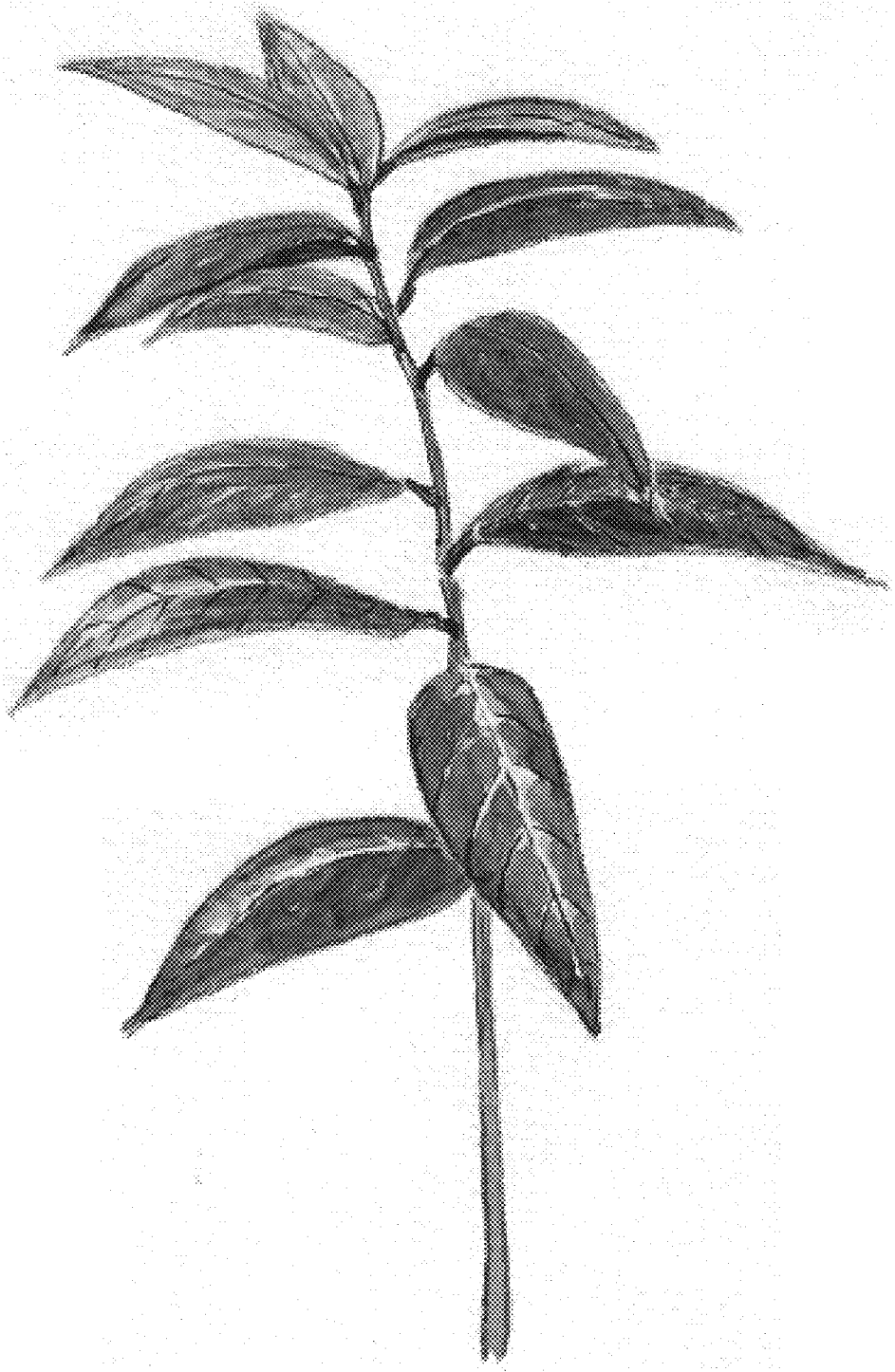
FIG. 4 illustrates a known variety of *Leucothoë fontanesiana axillaris*, the original stock.

The initial evergreen bush of the present new and distinct plant variety of the present invention was obtained by mutation of *L. fontanesiana axillaris* as follows: Cuttings of *L. fontanesiana axillaris* started in May, 1986 were rooted and tranplanted to vinyl pots (9 cm diameter) in October, 1986. On May 20, 1987 (next year) they were again transplanted to larger vinyl pots (12 cm diameter). Among 5,500 transplants, one plant was found to hold a mutated branch having leaves mottled with a variety of distinct colors such as red, yellow, and green, while other branches had dark green leaves as those of the parent plant (*L. fontanesiana axillaris*). Soon, the branch was taken for cutting and, in the spring of 1996, 5,000 new plants were produced.

The following is a detailed description of the new variety made from the observation of specimens grown in Kochi-prefecture, Japan. The color terminology used is in accordance with the Royal Horticultural Society Colour Chart.

Growth: The plants became matured, becoming about 40 cm tall, in two to three years after cutting in the inventor's climate (Kochi-prefecture, Japan).

*Height.—Up to* 0.6 m.

Parentage: *Leucothoë fontanesiana axillaris.*

Foliage: Similar to the leaves of known stocks of *Leucothoë axillaris*, the leaves of the new variety of the present invention have pointed tips and smooth edges.

*Size.*—The leaves are about 9-10 cm long, but the length can reach 11 cm. The width of the leaves ranges from about 1 cm to 3 cm.

*Color.*—The new variety has colorful leaves which are red, yellow and green throughout all seasons. The upper surfaces of immature leaves are red near 43B, 44B, 45D, 46A, 47A, 47B, 51A or 58A, occasionally mixed with areas of pink near 50C, 62B, 66C, 66D, 68D or 77D, but on rare occasion mixed with small areas of orange near 28A or 31B. As the leaves mature, the red color fades and the upper surfaces of the leaves either (a) appear yellow near 2B, 2C, 3B, 3D, 4A, 4B, 4C, 4D, 5C, 5D, 6D, 7D, 8C, 9C or 10C, mottled with green near 134B, 134C, 140A, 140B, 140C or 149B, optionally having a small red area at the apex and the margins near the apex, or (b) appear green near 134B, 134C, 140A, 140B, 140C or 149B having yellow margins near 2B, 2C, 3B, 3C, 3D, 4A, 4B, 4C, 4D, 5C, 5D, 6D, 7D, 8C, 9C or 10C. The upper surfaces of very mature leaves lose the yellow color and take on a darker green color near 136B, 137A, 137C, or 139A, optionally mixed with patches of green near 140A, 140B, 140C, 142B or 142C.

Branching: The plant spreads branches horizontally. The branches extend outward from the lower part of the stem, with each forming an arch.

Wood and bark: The wood and bark of the new variety have similar appearances as that of known stock of *Leucothoë fontanesiana axillaris.*

Flowers: The new variety seldom blooms. When the new variety blooms, the flowers are inconspicuous. On a few occasions when the new variety did bloom, small flowers clustering at the leaf axilla were observed, but the flowers soon died out without forming fruits.

Hardiness: The new variety may be grown between the south of Kanto to southern Kyushu in Japan, where the temperature ranges from about −5° C to 35° C, without protection during winter. The best location for growing the plant in Japan is the southern part of Shikoku. The plant needs full sun and fertile soil for good growth. Additionally, the plant seldom sufers from disease or insect damage.

Propagation: The new variety of the present invention can be asexually reproduced by either layering or cutting, but cutting is best. Rooting rate is over 90% if treated with mist. The preferred season for cutting is from April to July. Most preferably, cutting should be done between late May to early July.

The new variety of the present invention was asexually reproduced by cuttings treated with mist in Kochi-prefecture, Japan. It was observed that the distinguishing traits remained stable and true after such reproduction.

I claim:

1. A new and distinct variety of Leucothoë plant substantially as herein described and illustrated, having leaves which exhibit a tricolor appearance.

* * * * *